(12) United States Patent
Sugaya et al.

(10) Patent No.: US 8,382,973 B2
(45) Date of Patent: Feb. 26, 2013

(54) METHOD AND APPARATUS FOR CONTROLLING MULTI-GAS SENSOR

(75) Inventors: Satoshi Sugaya, Aichi (JP); Shiro Kakimoto, Aichi (JP); Tetsuo Yamada, Aichi (JP); Wataru Matsutani, Aichi (JP); Takio Kojima, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 258 days.

(21) Appl. No.: 12/874,113

(22) Filed: Sep. 1, 2010

(65) Prior Publication Data

US 2011/0048970 A1 Mar. 3, 2011

(30) Foreign Application Priority Data

Sep. 3, 2009 (JP) ................................. 2009-203303

(51) Int. Cl.
*G01N 27/41* (2006.01)
(52) U.S. Cl. ..................... 205/781; 205/784.5; 204/424; 73/23.31; 73/23.32
(58) Field of Classification Search .......... 204/421–429; 205/781–785; 73/23.31, 23.32
See application file for complete search history.

(56) References Cited

U.S. PATENT DOCUMENTS

| 6,332,965 | B1 * | 12/2001 | Sugiyama et al. ............ 204/425 |
| 2007/0079597 | A1 | 4/2007 | Wang et al. |
| 2007/0080074 | A1 | 4/2007 | Wang et al. |
| 2008/0110769 | A1 * | 5/2008 | Wang et al. ................... 205/781 |
| 2009/0301878 | A1 * | 12/2009 | Wang et al. ................... 204/429 |
| 2009/0308747 | A1 | 12/2009 | Cramer et al. |

FOREIGN PATENT DOCUMENTS

| DE | 10 2006 013 698 A1 | 9/2007 |
| DE | 10 2006 034 117 A1 | 1/2008 |
| EP | 0 878 709 A2 | 11/1998 |
| EP | 1 921 444 A1 | 5/2008 |
| JP | 2001-133447 A | 5/2001 |
| JP | 2009-511859 A | 3/2009 |
| JP | 2010-38806 A | 2/2010 |

* cited by examiner

*Primary Examiner* — J. Christopher Ball
*Assistant Examiner* — Jennifer Dieterle
(74) *Attorney, Agent, or Firm* — Sughrue Mion, PLLC

(57) ABSTRACT

A method and apparatus for controlling a multi-gas sensor, including an $NO_X$ sensor section and an ammonia sensor section. The $NO_X$ sensor section includes a first pumping cell adapted to pump oxygen into or out of a gas under measurement introduced into a first measurement chamber, and a second pumping cell communicating with the first measurement chamber and configured such that a second pumping current Ip2 corresponds to an $NO_X$ concentration of the gas under measurement. Oxygen concentration is calculated on the basis of a first pumping current flowing through the first pumping cell, and a corrected ammonia concentration is calculated on the basis of the oxygen concentration and the ammonia concentration output of the ammonia sensor section.

5 Claims, 9 Drawing Sheets

FIG. 4

63a — EXPRESSION REPRESENTING RELATION BETWEEN FIRST PUMPING CURRENT AND OXYGEN CONCENTRATION

63b — EXPRESSION REPRESENTING RELATION BETWEEN AMMONIA CONCENTRATION OUTPUT AND AMMONIA CONCENTRATION FOR EACH OXYGEN CONCENTRATION

63c — EXPRESSION REPRESENTING RELATION BETWEEN SECOND PUMPING CURRENT AND NO CONCENTRATION FOR EACH AMMONIA CONCENTRATION

63d — EXPRESSION REPRESENTING RELATION BETWEEN NEGATIVE AMMONIA CONCENTRATION OUTPUT AND $NO_2$ CONCENTRATION

63e — EXPRESSION REPRESENTING RELATION BETWEEN FRACTIONAL SECOND PUMPING CURRENT, AND NO CONCENTRATION AND $NO_2$ CONCENTRATION

63f — EXPRESSION REPRESENTING RELATION BETWEEN AMMONIA CONCENTRATION OUTPUT AND AMMONIA CONCENTRATION FOR EACH OXYGEN CONCENTRATION AND EACH $NO_2$ CONCENTRATION

METHOD AND APPARATUS FOR CONTROLLING MULTI-GAS SENSOR

BACKGROUND OF THE INVENTION

1. Field of the Invention

The present invention relates to a method and apparatus for controlling a multi-gas sensor suitable for detection of nitrogen oxide concentration and ammonia concentration of a gas under measurement.

2. Description of the Related Art

Known gas sensors for measuring the concentration of a specific gas contained in the exhaust gas of an automobile include an $NO_X$ sensor which employs a solid electrolyte body so as to detect the $NO_X$ concentration of a gas under measurement, and an ammonia sensor which detects the ammonia concentration of the gas under measurement by making use of a change in impedance between a pair of electrodes or a change in electromotive force generated therebetween.

Also, a technique has been proposed for simultaneously measuring the $NO_X$ concentration and ammonia concentration of a gas under measurement. The proposed technique has a step in which the gas under measurement is brought into contact with an $NH_3$ strong oxidizing catalyst so as to convert ammonia to $NO_X$, and the overall $NO_X$ concentration is measured; and a step in which the gas under measurement is brought into contact with an $NH_3$ weak oxidizing catalyst so as to convert a portion of ammonia to $NO_X$, and the $NO_X$ concentration is measured. The $NO_X$ concentration and the ammonia concentration are calculated from two detection values obtained in these steps (see Patent Document 1).

Furthermore, an ammonia sensor has been proposed in which an $NO_X$ electrode, a reference electrode, a selection electrode, and an ammonia electrode are provided in a single sensor to thereby form a plurality of cells. The method of calculating ammonia concentration is changed in accordance with an electromotive force generated between the $NO_X$ electrode and the reference electrode as a result of introduction of a gas (depending on the presence of $NO_X$), whereby the ammonia concentration is accurately measured (see Patent Document 2). Specifically, depending on the presence of $NO_X$, an electromotive force between the ammonia electrode and the reference electrode or an electromotive force between the $NO_X$ electrode and the ammonia electrode is selectively used for detection.

[Patent Document 1] Japanese Patent Application Laid-Open (kokai) No. 2001-133447 (abstract)
[Patent Document 2] Japanese Kohyo (PCT) Patent Publication No. 2009-511859 (abstract)

3. Problems to be Solved by the Invention

However, in the case of the technique described in Patent Document 1, since measurement is performed on the basis of a difference in catalytic performance, if the catalytic performance changes due to changes in measurement conditions (temperature, flow rate, pressure, etc.), accurate measurement cannot be performed. Moreover, in the case where the apparatus of Patent Document 1 is disposed in a severe environment such as in the exhaust gas of an automobile, it is difficult to stably maintain catalytic performance over a long period of time.

Also, the technique which is described in Patent Document 2 and in which the detection electrodes to be used for measuring ammonia concentration are switched has the following problem. When the measurement environment changes, initially set conditions for switching the detection electrodes (setting of switching timing, reference output point, etc.) must be changed, and accurate measurement of ammonia concentration becomes rather difficult. Furthermore, control, i.e., switching of the detection electrodes, is complicated.

Furthermore, in the case where a plurality of gas concentrations are measured using separate sensors, the following problem occurs. Since the sensors are not provided at the same location, gas concentration, temperature distribution, etc., vary among the sensors, and measurement delay occurs in certain of such sensors. The variation and delay may adversely affect the measurement.

Moreover, oxygen concentration may influence the measurement of ammonia concentration using an ammonia sensor. In particular, conventional ammonia sensors encounter difficulty due to the influence of oxygen concentration in measuring ammonia concentration.

SUMMARY OF THE INVENTION

Accordingly, an object of the present invention is to provide a method and apparatus for controlling a multi-gas sensor which can measure $NO_X$ concentration and ammonia concentration using a single gas sensor, and which can improve accuracy in measurement of ammonia concentration.

The above object of the present invention has been achieved by providing, in a first aspect (1), a method for controlling a multi-gas sensor, the multi-gas sensor comprising an $NO_X$ sensor section; and an ammonia sensor section formed on an outer surface of the $NO_X$ sensor section, wherein the $NO_X$ sensor section includes a first pumping cell which has paired first electrodes provided on a first solid electrolyte body such that the paired first electrodes are located on both the interior and exterior of a first measurement chamber, respectively, and is adapted to pump oxygen into or out of a gas under measurement introduced into the first measurement chamber, and a second pumping cell which has paired second electrodes provided on a second solid electrolyte body such that the paired second electrodes are located on both the interior and exterior of an $NO_X$ measurement chamber communicating with the first measurement chamber, respectively, and is configured such that a second pumping current flows between the paired second electrodes, the second pumping current corresponding to an $NO_X$ concentration of the gas under measurement having flowed into the $NO_X$ measurement chamber after adjustment of its oxygen concentration in the first measurement chamber; and the ammonia sensor section has at least a pair of electrodes formed on a solid electrolyte body and outputs an ammonia concentration output. The method comprises calculating an oxygen concentration on the basis of a first pumping current flowing through the first pumping cell; and calculating a corrected ammonia concentration on the basis of the oxygen concentration and the ammonia concentration output of the ammonia sensor section.

According to this method, the ammonia concentration can be accurately calculated without being affected by the oxygen concentration of the gas under measurement.

Furthermore, even in a severe environment, such as in the exhaust gas of an automobile, the ammonia concentration can be calculated stably over a long period of time.

Moreover, since the $NO_X$ sensor section and the ammonia sensor section are located at the same position, the sensor sections are placed under the same conditions (gas concentration, temperature distribution, etc.), whereby a measurement delay occurring in certain conventional sensors can be suppressed.

In a preferred embodiment (2) of the method (1) for controlling a multi-gas sensor, in the case where the ammonia concentration output of the ammonia sensor section becomes 0 as a result of setting the ammonia concentration of the gas under measurement to 0, said method comprises calculating a first corrected NO concentration on the basis of the corrected ammonia concentration and the second pumping current.

In the case where the gas under measurement contains ammonia gas and $NO_X$ gas (NO, $NO_2$), the second pumping current corresponding to the $NO_X$ concentration is affected by the ammonia concentration. However, by virtue of the present embodiment (2), the $NO_X$ concentration can be detected accurately without being affected by the ammonia concentration.

Notably, this preferred embodiment (2) is used when the gas under measurement does not contain $NO_2$, and the NO concentration can be accurately calculated without being affected by the ammonia concentration of the gas under measurement.

An example of the "time when the ammonia concentration of the gas under measurement is set to 0" is when a predetermined period of time has elapsed after injection of aqueous urea into the gas under measurement has stopped. The circumstance in which the ammonia concentration becomes 0 at that time is utilized. Further, the above-described method is used in the case where, when the ammonia concentration is measured by the ammonia sensor section exposed to the gas under measurement, the ammonia concentration output becomes 0.

In a preferred embodiment (3) of the method (1) for controlling a multi-gas sensor, in the case where the ammonia concentration output of the ammonia sensor section becomes negative as a result of setting the ammonia concentration of the gas under measurement to 0, said method comprises calculating an expected $NO_2$ concentration in advance on the basis of the negative ammonia concentration output, and calculating a second corrected NO concentration on the basis of the second pumping current and the expected $NO_2$ concentration.

In the case where the gas under measurement contains ammonia gas and $NO_X$ gas (NO, $NO_2$), the second pumping current corresponding to the $NO_X$ concentration is affected by the ammonia concentration. However, by virtue of the present embodiment (3), the $NO_X$ concentration can be accurately detected without being affected by the ammonia concentration.

Notably, this preferred embodiment (3) is used when the gas under measurement contains $NO_2$, and, even in the case where NO and $NO_2$ coexist in the gas under measurement, the NO concentration and the $NO_2$ concentration can be calculated separately and accurately. In contrast, in conventional $NO_X$ sensors, separation of NO and $NO_2$ is difficult. In addition, NO and $NO_2$ differ in molecular size. Therefore, even in the case where the above-mentioned second pumping current of the $NO_X$ sensor is the same, the calculated $NO_X$ concentration may change in accordance with the ratio between NO and $NO_2$ in the gas under measurement.

An example of the "time when the ammonia concentration of the gas under measurement is set to 0" is a time when a predetermined period of time has elapsed after injection of aqueous urea into the gas under measurement has stopped. The circumstance in which the ammonia concentration becomes 0 at that time is utilized. Further, the above-described method is used in the case where, when the ammonia concentration is measured by the ammonia sensor section exposed to a gas under measurement containing $NO_2$, the ammonia concentration output becomes negative at that time.

In a preferred embodiment (4) of the method (3) for controlling a multi-gas sensor, the method comprises calculating the corrected ammonia concentration on the basis of the expected $NO_2$ concentration as well as the oxygen concentration.

According to the preferred embodiment (4), the ammonia concentration is calculated in consideration of not only the oxygen concentration but also the $NO_2$ concentration. Therefore, the measurement accuracy is further improved as compared with the case where the ammonia concentration is calculated in consideration of the oxygen concentration alone.

In a second aspect (5), the present invention also provides an apparatus for controlling a multi-gas sensor, the multi-gas sensor comprising an $NO_X$ sensor section; and an ammonia sensor section formed on an outer surface of the $NO_X$ sensor section, wherein the $NO_X$ sensor section includes a first pumping cell which has paired first electrodes provided on a first solid electrolyte body such that the paired first electrodes are located on both the interior and exterior of a first measurement chamber, respectively, and is adapted to pump oxygen into or out of a gas under measurement introduced into the first measurement chamber, and a second pumping cell which has paired second electrodes provided on a second solid electrolyte body such that the paired second electrodes are located on both the interior and exterior of an $NO_X$ measurement chamber communicating with the first measurement chamber, respectively, and is configured such that a second pumping current flows between the paired second electrodes, the second pumping current corresponding to an $NO_X$ concentration of the gas under measurement having flowed into the $NO_X$ measurement chamber after adjustment of its oxygen concentration in the first measurement chamber; and the ammonia sensor section has at least a pair of electrodes formed on a solid electrolyte body and outputs an ammonia concentration output. The apparatus comprises control means for calculating an oxygen concentration on the basis of a first pumping current flowing through the first pumping cell, and for calculating a corrected ammonia concentration on the basis of the oxygen concentration and the ammonia concentration output of the ammonia sensor section.

According to this apparatus, the ammonia concentration can be calculated accurately without being affected by the oxygen concentration of the gas under measurement.

Furthermore, even in a severe environment, such as in the exhaust gas of an automobile, the ammonia concentration can be calculated stably over a long period of time.

Moreover, since the $NO_X$ sensor section and the ammonia sensor section are located at the same position, the sensor sections are subject to the same conditions (gas concentration, temperature distribution, etc.), whereby a measurement delay occurring in certain conventional sensors can be suppressed.

Effect of the Invention

In accordance with the present invention, $NO_X$ concentration and ammonia concentration may be measured using a single gas sensor, and with improved accuracy in measurement of ammonia concentration.

BRIEF DESCRIPTION OF THE DRAWINGS

FIG. 4 is a block diagram showing the configuration of various data stored in the gas sensor control apparatus (a microcomputer thereof).

DESCRIPTION OF REFERENCE NUMERALS AND SYMBOLS

Figure 1:
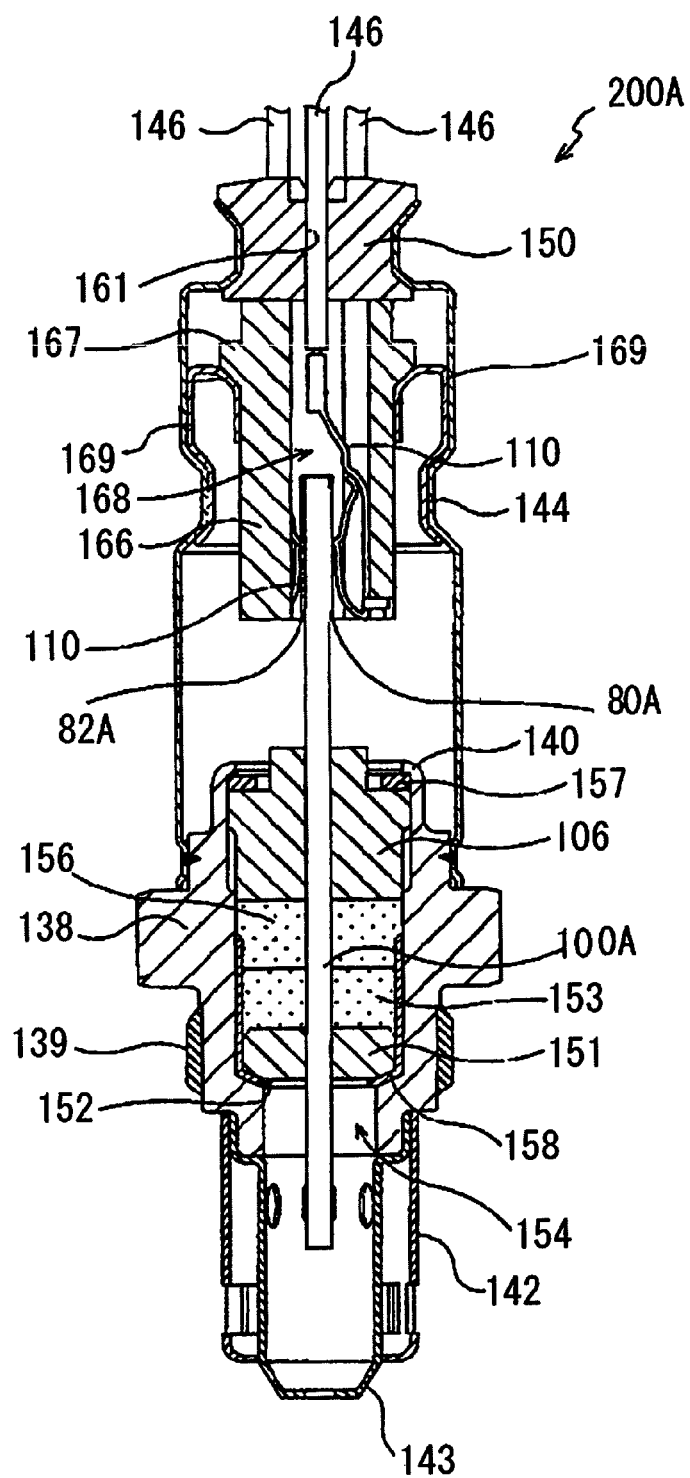
FIG. 1 is a longitudinal sectional view of a multi-gas sensor according to an embodiment of the present invention.

Reference numerals used to identify various structural features in the drawings include the following.

| | |
|---|---|
| 2a: | first solid electrolyte body |
| 2b, 2c: | first electrode (inner first pumping electrode, outer first pumping electrode) |
| 2: | first pumping cell |
| 4a: | second solid electrolyte body |
| 4b, 4c: | second electrode (inner second pumping electrode, second pumping counter electrode) |
| 4: | second pumping cell |
| 25: | solid electrolyte body for ammonia sensor section |
| 30A: | $NO_X$ sensor section |
| 42: | ammonia sensor section |
| 42a: | pair of electrodes |
| 42b: | selective reaction layer |
| 44A, 44B: | diffusion layer |
| 60, 61: | control means (CPU of microcomputer) |
| 100A: | multi-gas sensor element section |
| 200A: | multi-gas sensor |
| 300: | multi-gas sensor control apparatus |
| S1: | first measurement chamber |
| S2: | $NO_X$ measurement chamber |
| Ip1: | first pumping current |
| Ip2: | second pumping current |

DETAILED DESCRIPTION OF THE PREFERRED EMBODIMENTS

An embodiment of the present invention will next be described with reference to the drawings. However, the present invention should not be construed as being limited thereto.

FIG. 1 shows a longitudinal cross section of a multi-gas sensor 200A, which is an example sensor to be controlled by a control method according to the embodiment of the present invention. The multi-gas sensor 200A is an assembly including a multi-gas sensor element section 100A for detecting ammonia concentration and $NO_X$ concentration. The multi-gas sensor 200A includes the plate-shaped multi-gas sensor element section 100A extending in an axial direction; a tubular metallic shell 138 having a threaded portion 139 formed on an outer surface thereof for mounting to an exhaust pipe; a tubular ceramic sleeve 106 disposed to surround the circumference of the multi-gas sensor element section 100A; an insulating contact member 166 disposed such that the inner wall surface of a contact insertion hole 168 axially extending through the insulating contact member 166 surrounds the circumference of a rear end portion of the multi-gas sensor element section 100A; and a plurality of connection terminals 110 (in FIG. 1, only two connection terminals are illustrated) disposed between the multi-gas sensor element section 100A and the insulating contact member 166.

The metallic shell 138, which is formed into a generally tubular shape, has a through hole 154 axially extending through the metallic shell 138, and a ledge portion 152 projecting radially inward from the wall surface of the through hole 154. The metallic shell 138 holds the multi-gas sensor element section 100A in the through hole 154 such that a front end portion of the multi-gas sensor element section 100A is located frontward of the front end of the through hole 154, and electrode terminal portions 80A and 82A are located rearward of the rear end of the through hole 154. The ledge portion 152 has an inwardly tapered surface which inclines in relation to a plane perpendicular to the axial direction.

A ceramic holder 151, powder layers 153 and 156 (hereinafter also referred to as "talc rings 153 and 156"), and the above-mentioned ceramic sleeve 106 are stacked in the through hole 154 of the metallic shell 138, in this sequence from the front end side toward the rear end side, so that they surround the circumference of the multi-gas sensor element section 100A. A crimp packing 157 is disposed between the ceramic sleeve 106 and a rear end portion 140 of the metallic shell 138. A metallic holder 158 for holding the talc ring 153 and the ceramic holder 151 and for maintaining airtightness is disposed between the ceramic holder 151 and the ledge portion 152 of the metallic shell 138. Notably, the rear end portion 140 of the metallic shell 138 is crimped such that the rear end portion 140 presses the ceramic sleeve 106 frontward via the crimp packing 157.

Meanwhile, as shown in FIG. 1, an outer protector 142 and an inner protector 143, which are formed of metal (e.g., stainless steel) and form a double protector, are attached to the outer circumference of a front end portion (a lower end portion in FIG. 1) of the metallic shell 138 by means of, for example, welding. The outer protector 142 and the inner protector 143 cover a projecting portion of the multi-gas sensor element section 100A, and each has a plurality of holes.

An outer sleeve 144 is fixed to the outer circumference of a rear end portion of the metallic shell 138. A grommet 150 is disposed in an opening of the outer sleeve 144 located on the rear end side (on the upper side in FIG. 1) thereof. The grommet 150 has lead wire insertion holes 161, through which a plurality of lead wires 146 (only three of them are shown in FIG. 1) are inserted to be electrically connected to the electrode terminal portions 80A and 82A of the multi-gas sensor element section 100A. Notably, in FIG. 1, in order to simplify the drawing, electrode terminal portions on the front surface of the multi-gas sensor element section 100A and those on the back surface thereof are represented by the electrode terminal portions 80A and 82A, respectively. However, in actuality, a plurality of electrode terminal portions are formed on each surface in accordance with the numbers of electrodes, etc., of an $NO_X$ sensor section 30A and an ammonia sensor section 42, which will be described below.

The insulating contact member 166 is disposed at a rear end portion (an upper end portion in FIG. 1) of the multi-gas sensor element section 100A projecting from the rear end portion 140 of the metallic shell 138. The insulating contact member 166 is disposed to surround the electrode terminal portions 80A and 82A formed on the front and back surfaces of the multi-gas sensor element section 100A. The insulating contact member 166, which is formed into a tubular shape, has a contact insertion hole 168 axially extending through the insulating contact member 166, and a flange portion 167 projecting radially outward from an outer surface thereof. The insulating contact member 166 is disposed inside the outer sleeve 144 with its flange portion 167 being in contact with the outer sleeve 144 via a holding member 169. The connection terminals 110 disposed in the insulating contact member 166 are electrically connected to the electrode terminal portions 80A and 82A of the multi-gas sensor element section 100A, and electrically communicate with an external device via the lead wires 146.

Figure 2:
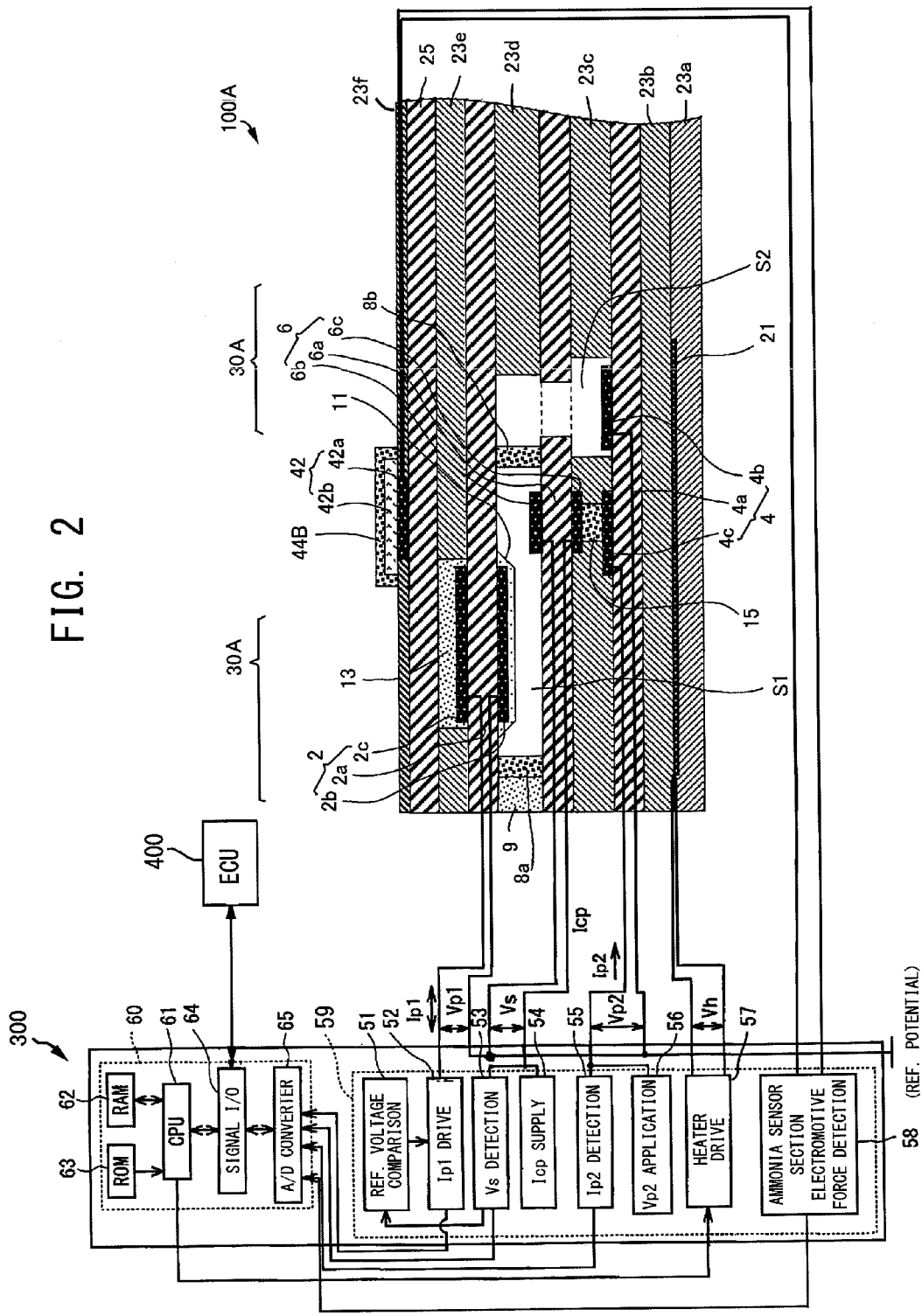
FIG. 2 is a block diagram showing the configuration of the multi-gas sensor and a gas sensor control apparatus according to the embodiment of the present invention.

FIG. 2 is a block diagram showing the configuration of a multi-gas sensor control apparatus (controller) 300 according to the embodiment of the present invention, and the configuration of the multi-gas sensor element section 100A connected thereto. Notably, in order to facilitate description, FIG. 2 shows only a longitudinal cross section of the multi-gas sensor element section 100A accommodated within the multi-gas sensor 200A.

The multi-gas sensor 200A (the multi-gas sensor element section 100A) and the multi-gas sensor control apparatus 300 are mounted on an unillustrated vehicle having an internal combustion engine (hereinafter also referred to as the "engine"), and the multi-gas sensor control apparatus 300 is electrically connected to a vehicle-side control apparatus (hereinafter also referred to as "ECU" or Electronic Control Unit) 400. Notably, ends of the lead wires 146 extending from the multi-gas sensor 200A are connected to a connector, which is electrically connected to a connector of the multi-gas sensor control apparatus 300.

The ECU 400 receives data representing the ammonia concentration and $NO_X$ concentration of exhaust gas calculated by the multi-gas sensor control apparatus 300, and executes various types of processing on the basis of the data thus received so as to control the operational status of the engine or remove $NO_X$ accumulated in a catalyst unit.

Next, the configuration of the multi-gas sensor element section 100A will be described. The multi-gas sensor element section 100A includes the $NO_X$ sensor section 30A having a configuration similar to that of a known $NO_X$ sensor, and the ammonia sensor section 42 having a configuration similar to that of a known ammonia sensor. As described in detail below, the ammonia sensor section 42 is formed on the outer surface of the $NO_X$ sensor section 30A.

The $NO_X$ sensor section 30A includes insulating layers 23f, a solid electrolyte body 25 for the ammonia sensor section, an insulating layer 23e, a first solid electrolyte body 2a, an insulating layer 23d, a third solid electrolyte body 6a, an insulating layer 23c, a second solid electrolyte body 4a, and insulating layers 23b and 23a, which are stacked in this sequence. A first measurement chamber S1 is formed between the first solid electrolyte body 2a and the third solid electrolyte body 6a. A gas under measurement is externally introduced into the first measurement chamber S1 via a first diffusion resistance 8a disposed at the left end (inlet) of the first measurement chamber S1. Notably, a protection layer 9 formed of a porous material is disposed on the outer side of the first diffusion resistance 8a.

A second diffusion resistance 8b is disposed at the end of the first measurement chamber S1 opposite the inlet. A second measurement chamber (corresponding to the "$NO_X$ measurement chamber" of the present invention) S2 is defined on the right side of the first measurement chamber S1, and communicates with the first measurement chamber S1 via the second diffusion resistance 8b. The second measurement chamber S2 is formed between the first solid electrolyte body 2a and the second solid electrolyte body 4a such that the second measurement chamber S2 penetrates the third solid electrolyte body 6a.

An elongated plate-shaped heater 21 is embedded between the insulating layers 23b and 23a such that the heater 21 extends along the longitudinal direction of the multi-gas sensor element section 100A. The heater 21 heats the gas sensor to an activation temperature and enhances the oxygen ion conductivity of the solid electrolyte body, thereby stabilizing its operation.

Each of the insulating layers 23a, 23b, 23c, 23d, 23e and 23f is mainly formed of alumina. Each of the first diffusion resistance 8a and the second diffusion resistance 8b is formed of a porous material such as alumina. The heater 21 is formed of platinum or the like.

A first pumping cell 2 includes a first solid electrolyte body 2a mainly formed of zirconia having oxygen ion conductivity; and inner and outer (counter) first pumping electrodes 2b and 2c (corresponding to the "first electrodes" of the invention) disposed to sandwich the first solid electrolyte body 2a. The inner first pumping electrode 2b faces the first measurement chamber S1. Each of the inner and outer first pumping electrodes 2b and 2c is mainly formed of platinum, and the surface of the inner first pumping electrode 2b is covered with a protection layer 11 formed of a porous material.

A portion of the insulating layer 23e corresponding to the upper surface of the outer first pumping electrode 2c is removed so as to form an opening, and the opening is filled with a porous material 13. Thus, communication is established between the outer first pumping electrode 2c and the exterior of the sensor element section, to thereby permit entry and exit of gas (oxygen).

An oxygen concentration detection cell 6 includes a third solid electrolyte body 6a mainly formed of zirconia; and a detection electrode 6b and a reference electrode 6c disposed to sandwich the third solid electrolyte body 6a. The detection electrode 6b faces the first measurement chamber S1 at a position downstream of the inner first pumping electrode 2b. Each of the detection electrode 6b and the reference electrode 6c is mainly formed of platinum.

Notably, the insulating layer 23c is partially removed so as to from an opening such that the reference electrode 6c in contact with the third solid electrolyte body 6a is disposed in the opening. The opening is filled with a porous material, and forms a reference oxygen chamber 15. When a very weak constant current is supplied to the oxygen concentration detection cell 6 from an Icp supply circuit 54, the oxygen concentration detection cell 6 supplies oxygen from the first measurement chamber S1 to the reference oxygen chamber 15, to thereby establish an oxygen reference.

A second pumping cell 4 includes a second solid electrolyte body 4a mainly formed of zirconia; and an inner second pumping electrode 4b and a second pumping counter electrode 4c (corresponding to the "second electrodes" of the invention) disposed on the surface of the second solid electrolyte body 4a facing the second measurement chamber S2.

Each of the inside second pumping electrode 4b and the second pumping counter electrode 4c is mainly formed of platinum.

Notably, the second pumping counter electrode 4c is disposed on the second solid electrolyte body 4a to be located in the opening of the insulating layer 23c. Therefore, the second pumping counter electrode 4c faces the reference electrode 6c via the reference oxygen chamber 15.

The inner first pumping electrode 2b, the detection electrode 6b, and the inner second pumping electrode 4b are connected to a reference potential.

The ammonia sensor section 42 is formed on the insulating layers 23f, which form the outer surface of the $NO_X$ sensor section 30A. However, the insulating layers 23f are partially removed such that the solid electrolyte body 25 for the ammonia sensor section is exposed; and a pair of electrodes 42a of the ammonia sensor section 42 are formed on the exposed portion. More specifically, the ammonia sensor section 42 includes the pair of electrodes 42a formed on the solid electrolyte body 25 for the ammonia sensor section, and a selective reaction layer 42b which covers the pair of electrodes 42a. The ammonia sensor section 42 detects the ammonia concentration of the gas under measurement from a change in electromotive force between the pair of electrodes 42a.

A diffusion layer 44B formed of a porous material is configured so as to completely cover the selective reaction layer 42b. The diffusion layer 44B can adjust the diffusion speed of the gas under measurement which flows into the ammonia sensor section 42 from outside the sensor element section.

Figure 3:
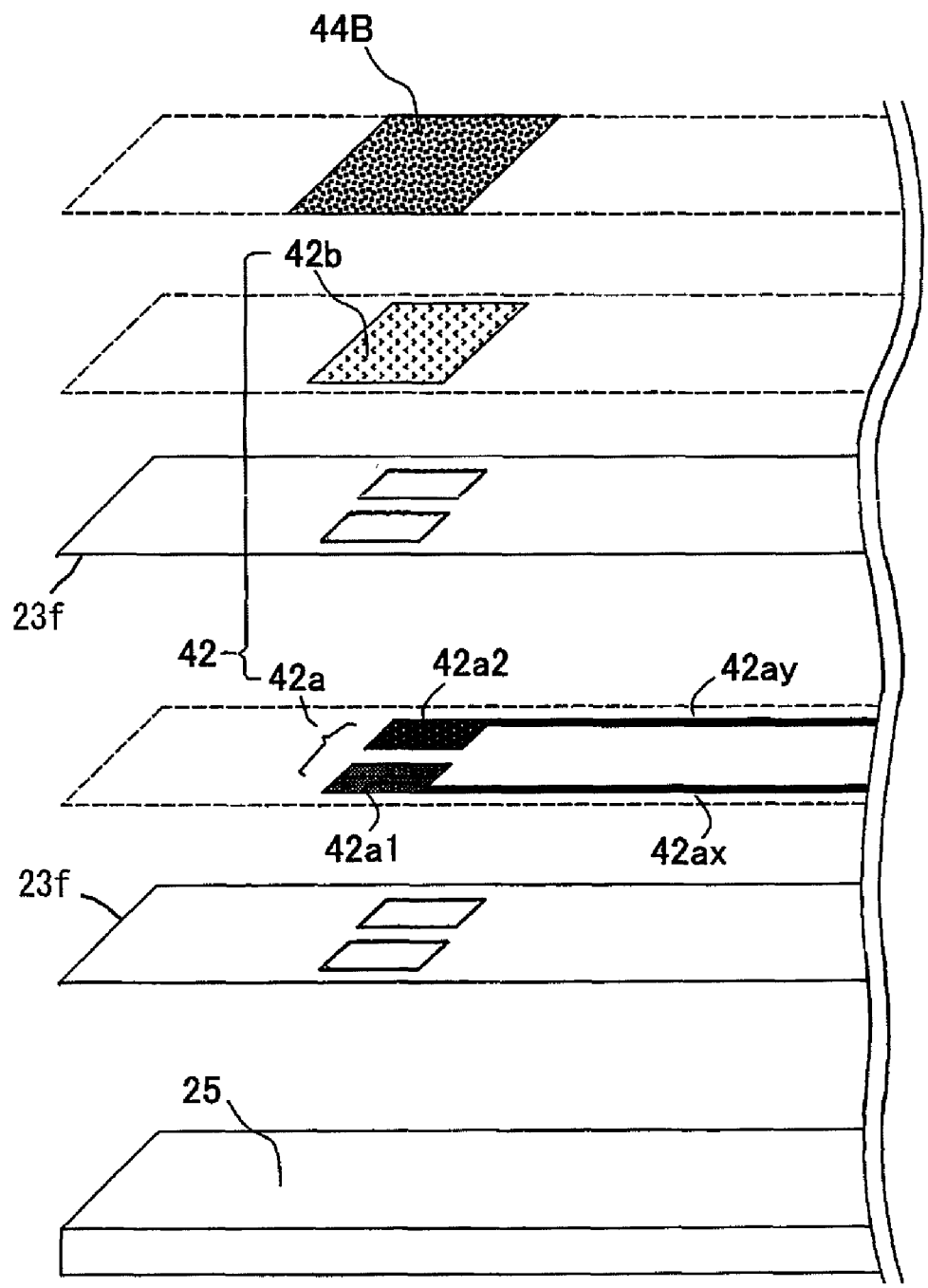
FIG. 3 is an exploded view showing the configuration of an ammonia sensor section.

FIG. 3 is an exploded view showing the configuration of the ammonia sensor section 42. Paired electrodes 42a1 and 42a2 (the pair of electrodes 42a) are disposed on the solid electrolyte body 25 for the ammonia sensor section. Leads 42ax and 42ay extend from the electrodes 42a1 and 42a2 along the longitudinal direction of the solid electrolyte body 25 for the ammonia sensor section. The upper and lower sides of the leads 42ax and 42ay are covered with the insulating layers 23f. Right end portions of the leads 42ax and 42ay are not covered with the insulating layers 23f and are exposed to the outside to thereby form predetermined electrode terminal portions.

The electrodes 42a1 and 42a2 are juxtaposed and spaced from each other along the lateral direction of the solid electrolyte body 25 for the ammonia sensor section. The electrode 42a1 is formed of a material whose main component is gold, and functions as a detection electrode. The electrode 42a2 is formed of a material whose main component is platinum, and functions as a reference electrode. Since the detection electrode 42a1 has a higher reactivity with ammonia than the reference electrode 42a2, an electromotive force is produced between the detection electrode 42a1 and the reference electrode 42a2.

The solid electrolyte body 25 for the ammonia sensor section is formed of an oxygen-ion-conductive material such as $ZrO_2$. The leads 42ax and 42ay are formed, for example, of a material whose main component is platinum.

The selective reaction layer 42b has a function of burning combustible gas components of the gas under measurement, other than ammonia. When the selective reaction layer 42b is present, ammonia contained in the gas under measurement can be detected without being affected by combustible gas components. The selective reaction layer 42b generally includes a metal oxide as a main component, and is preferably formed from a material (e.g., bismuth vanadium oxide: $BiVO_4$) which contains vanadium oxide ($V_2O_5$) and bismuth oxide ($Bi_2O_3$) in predetermined proportions.

Notably, the above-described effect can be attained even when the selective reaction layer 42b covers the detection electrode 42a1 alone. In the present embodiment, the detection electrode 42a1 and the selective reaction layer 42b are separately provided. However, the embodiment may be modified such that the selective reaction layer 42b is not provided, and a material (e.g., a metal oxide) which forms the selective reaction layer 42b is included in the detection electrode 42a1.

The diffusion layer 44B is formed, for example, of at least one selected from the group consisting of alumina, spinel ($MgAl_2O_4$), silica alumina and mullite. The diffusion time required for the gas to reach the selective reaction layer 42b and the electrodes 42a1 and 42a2 can be adjusted by adjusting the thickness, grain size, size distribution, porosity, compositional proportions, etc., of the diffusion layer 44B.

Notably, in the present embodiment, the position of the ammonia sensor section 42 on the $NO_X$ sensor section 30A is determined such that, when the controlled temperature of the second solid electrolyte body 4a of the $NO_X$ sensor section 30A is set to 600° C., the temperature of the ammonia sensor section 42 becomes 650° C.

Referring back to FIG. 2, an example configuration of the multi-gas sensor control apparatus 300 will be described. The multi-gas sensor control apparatus 300 includes an (analog) control circuit 59 and a microcomputer 60 provided on a circuit board. The microcomputer 60, which controls the entire multi-gas sensor control apparatus 300, includes a CPU (Central Processing Unit) 61, a RAM 62, a ROM 63, a signal input/output section 64, an A/D converter 65, and an unillustrated clock. The CPU executes programs stored in the ROM, etc., in advance.

The control circuit 59 includes a reference voltage comparison circuit 51, an Ip1 drive circuit 52, a Vs detection circuit 53, an Icp supply circuit 54, an Ip2 detection circuit 55, a Vp2 application circuit 56, a heater drive circuit 57, and an ammonia sensor section electromotive force detection circuit 58, described in detail below.

The control circuit 59 controls the $NO_X$ sensor section 30A, detects first and second pumping currents Ip1 and Ip2 flowing through the $NO_X$ sensor section 30A, and outputs the detected first and second pumping currents Ip1 and Ip2 to the microcomputer 60.

The ammonia sensor section electromotive force detection circuit 58 detects an ammonia concentration output (electromotive force) between the paired electrodes 42a1 and 42a2, and outputs the detected ammonia concentration output to the microcomputer 60.

Specifically, the outer first pumping electrode 2c of the $NO_X$ sensor section 30A is connected to the Ip1 drive circuit 52, and the reference electrode 6c is connected to the Vs detection circuit 53 and the Icp supply circuit 54. The second pumping counter electrode 4c is connected to the Ip2 detection circuit 55 and the Vp2 application circuit 56. The heater circuit 57 is connected to the heater 21.

The paired electrodes 42a1 and 42a2 of the ammonia sensor section 42 are connected to the ammonia sensor section electromotive force detection circuit 58.

The circuits 51 to 57 have the following functions.

The Ip1 drive circuit 52 supplies a first pumping current Ip1 which flows between the inner first pumping electrode 2b and the outer first pumping electrode 2c, and detects the first pumping current Ip1 at that time.

The Vs detection circuit 53 detects a voltage Vs between the detection electrode 6b and the reference electrode 6c, and outputs the detected voltage Vs to the reference voltage comparison circuit 51.

The reference voltage comparison circuit 51 compares a reference voltage (e.g., 425 mV) and the output (voltage Vs) of the Vs detection circuit 53, and outputs a comparison result to the Ip1 drive circuit 52. The Ip1 drive circuit 52 controls the flow direction and magnitude of the Ip1 current such that the voltage Vs becomes equal to the above-mentioned reference voltage, to thereby adjust the concentration of oxygen within the first measurement chamber S1 to a predetermined value at which $NO_X$ does not decompose.

The Icp supply circuit 54 supplies a weak current Icp which flows between the detection electrode 6b and the reference electrode 6c so as to pump oxygen from the first measurement chamber S1 into the reference oxygen chamber 15, to thereby expose the reference electrode 6c to oxygen of a predetermined concentration serving as a reference.

The Vp2 application circuit 56 applies between the inner second pumping electrode 4b and the second pumping counter electrode 4c a constant voltage Vp2 (e.g., 450 mV) at which $NO_X$ gas in the gas under measurement decomposes to oxygen and $N_2$ gas, to thereby decompose $NO_X$ to nitrogen and oxygen.

The Ip2 detection circuit 55 detects a second pumping current Ip2 which flows through the second pumping cell 4 when oxygen produced as a result of decomposition of $NO_X$ is pumped from the second measurement chamber S2 toward the second pumping counter electrode 4c via the second solid electrolyte body 4a.

The Ip1 drive circuit 52 outputs the value of the detected first pumping current Ip1 to the A/D converter 65. Furthermore, the Ip2 detection circuit 55 outputs the value of the detected second pumping current Ip2 to the A/D converter 65.

The A/D converter 65 converts these values to corresponding digital values, and outputs the digital values to the CPU 61 via the signal input/output section 64.

Next, an example control performed by the control circuit 59 will be described. First, when the control circuit 59 receives electric power from an external power supply upon startup of the engine, the heater 21 operates via the heater circuit 57 so as to heat the first pumping cell 2, the oxygen concentration detection 6, and the second pumping cell 4 to an activation temperature. The Icp supply circuit 54 supplies a weak current Icp which flows between the detection electrode 6b and the reference electrode 6c so as to pump oxygen from the first measurement chamber S1 into the reference oxygen chamber 15, to thereby create an oxygen reference.

When the $NO_X$ sensor section 30A is heated to a suitable temperature by the heater 21, the ammonia sensor section 42 on the $NO_X$ sensor section 30A is also heated to a desired temperature as well.

Once each cell has been heated to the activation temperature, the first pumping cell 2 pumps, from the inner first pumping electrode 2b toward the outer first pumping electrode 2c, oxygen contained in the gas under measurement (exhaust gas) having flowed into the first measurement chamber S1.

At that time, the oxygen concentration within the first measurement chamber S1 corresponds to the inter-electrode voltage (inter-terminal voltage) Vs of the oxygen concentration detection cell 6. Therefore, the Ip1 drive circuit 52 controls the first pumping current Ip1 flowing through the first pumping cell 2 such that the inter-electrode voltage Vs becomes equal to the above-mentioned reference voltage, to thereby adjust the oxygen concentration within the first measurement chamber S1 to a level at which $NO_X$ does not decompose.

The gas under measurement whose oxygen concentration has been adjusted flows toward the second measurement chamber S2. The Vp2 application circuit 56 applies to the second pumping cell 4, as an inter-electrode voltage (inter-terminal voltage), a constant voltage Vp2 (voltage higher than the control voltage of the oxygen concentration detection cell 6; e.g., 450 mV) at which $NO_X$ gas in the gas under measurement decomposes into oxygen and $N_2$ gas. Thus, $NO_X$ is decomposed into nitrogen and oxygen. Then, a second pumping current Ip2 flows through the second pumping cell 4 such that oxygen produced as a result of decomposition of $NO_X$ is pumped out from the second measurement chamber S2. Since a linear relation is present between the second pumping current Ip2 and the $NO_X$ concentration, the $NO_X$ concentration of the gas under measurement can be detected by detecting the second pumping current Ip2 by the Ip2 detection circuit 55. Notably, in the present invention, when necessary, a determination as to whether or not $NO_X$ includes $NO_2$ is made. Thus, the concentration of NO contained in $NO_X$ and the concentration of $NO_X$ can be calculated accurately and separately. Processing for calculating these concentrations will be described below.

Also, the ammonia sensor section electromotive force detection circuit 58 can detect the ammonia concentration output (electromotive force) between the paired electrodes 42a1 and 42a2 to thereby detect the ammonia concentration of the gas under measurement. Notably, the $NH_3$ concentration is calculated using an ammonia concentration conversion value which is stored in the microcomputer 60 and which is determined on the basis of the electromotive force between the electrodes 42a1 and 42a2 (a rate of change (sensitivity) between a base electromotive force at the time when the ammonia concentration is 0 and an electromotive force at the time when ammonia is present may be used). Processing for calculating the $NH_3$ concentration will be described below.

Next, the configurations of various data sets 63a to 63f stored in the microcomputer 60 (ROM 63) of the multi-gas sensor control apparatus 300 will be described with reference to FIG. 4. Notably, the CPU (corresponding to the "control means" of the invention) 61 reads the various data sets 63a to 63f, and executes processing for calculating various gas concentrations, such as ammonia concentration, as follows.

As shown in FIG. 4, the ROM 63 stores an expression 63a representing the relation between first pumping current (Ip1) and oxygen concentration; an expression 63b representing the relation between ammonia concentration output (electromotive force EMF) and ammonia concentration for each of a plurality of oxygen concentrations; an expression 63c representing the relation between second pumping current (Ip2) and NO concentration for each of a plurality of ammonia concentrations; an expression 63d representing the relation between negative ammonia concentration output and $NO_2$ concentration; an expression 63e representing the relation between fractional second pumping current, and NO concentration and $NO_2$ concentration; and an expression 63f representing the relation between ammonia concentration output and ammonia concentration for each combination between a plurality of oxygen concentrations and a plurality of $NO_2$ concentrations.

Notably, in the example of FIG. 4, each of the various data sets 63a to 63f represents a predetermined relational expression. However, each of the various data sets 63a to 63f may represent a table or the like so long as the table or the like enables calculation of various gas concentrations from the output of the sensor. Alternatively, each of the various data sets 63a to 63f may represent a relational expression, table, or the like which represents values obtained in advance by use of a model gas whose gas concentrations are known.

The relational expression 63a represents the relation between the first pumping current (Ip1), which flows through the first pumping cell 2 as a result of pumping oxygen into or out of the gas under measurement introduced into the first measurement chamber, and the oxygen concentration of the gas under measurement. Although not illustrated, in general, a substantially linear relation is present between Ip1 and the oxygen concentration. The oxygen concentration of the gas under measurement can be calculated on the basis of the relational expression 63a representing the relation between the first pumping current (Ip1) and the oxygen concentration.

The relational expression 63b is set for each of a plurality of oxygen concentrations, and represents the relation between the ammonia concentration output of the ammonia sensor section and the ammonia concentration of the gas under measurement.

Figure 5:
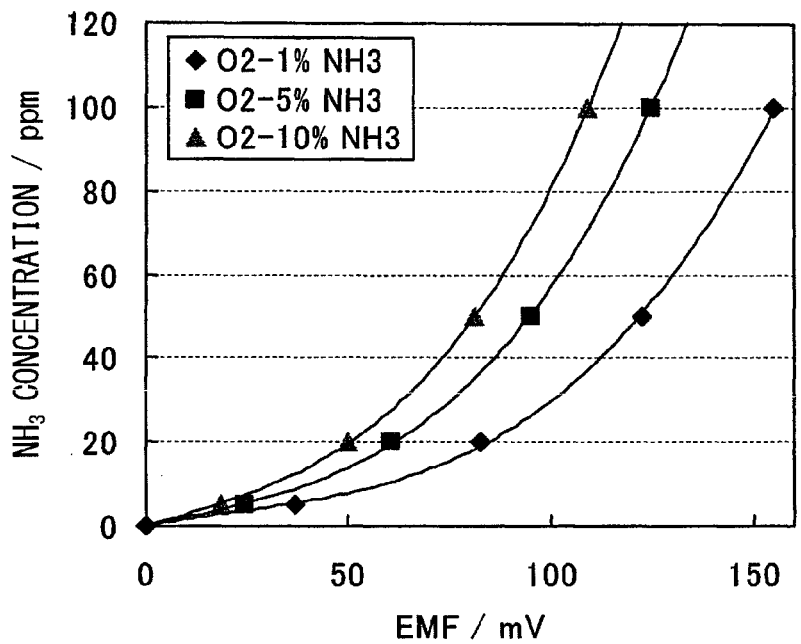
FIG. 5 is a graph showing an example expression representing the relation between ammonia concentration output and ammonia concentration.

FIG. 5 shows an example expression representing the relation between the ammonia concentration output and the ammonia concentration. In the present embodiment, for each of different oxygen concentrations, the ammonia concentration is represented by a third-order expression of EMF. EMF changes depending on oxygen concentration. However, since the ammonia concentration is determined from the relational expression 63b representing the relation between the ammonia concentration output and the ammonia concentration for each of a plurality of oxygen concentrations, an accurate value of the ammonia concentration (corresponding to the "corrected ammonia concentration" of the invention) which is not affected by the oxygen concentration of the gas under measurement can be calculated.

Notably, an expression representing the relation between the ammonia concentration output and the ammonia concentration for a certain oxygen concentration which has not been set can be calculated, through extrapolation, from the expressions representing the relation between the ammonia concentration output and the ammonia concentration for two set oxygen concentrations which are higher and lower than the certain oxygen concentration, respectively.

The relational expression 63c representing the relation between second pumping current and NO concentration is set for each of a plurality of ammonia concentrations. This relational expression is used in the case where the gas under measurement does not contain $NO_2$. In this case, when the ammonia concentration of the gas under measurement is set to 0, the ammonia concentration output of the ammonia sensor section becomes 0. In the case where the multi-gas sensor 200A is used in a urea SCR (Selective Catalytic Reduction) system, the "time when the ammonia concentration of the gas under measurement is set to 0" is, for example, a time when a predetermined period of time has elapsed after injection of aqueous urea has stopped. If the ammonia concentration output is 0 at such a timing, the CPU 61 determines that the gas under measurement does not contain $NO_2$, and executes processing in which the relational expression 63c is used. As described below, this timing is assumed to be a point in time when the ammonia gas concentration output has reached its lowest value. Specifically, values of the ammonia gas concentration output are stored in the RAM 62. When a value acquired at this time is greater than the value acquired the previous time by a predetermined value (determined in consideration of variation), the CPU 61 judges that a predetermined time has elapsed after the injection of aqueous urea has stopped. The CPU 61 determines the timing at which the lowest value among the values acquired up to the present time is acquired, as the "time when the ammonia concentration of the gas under measurement is set to 0," and determines whether the lowest value is 0 or negative.

Figure 6:
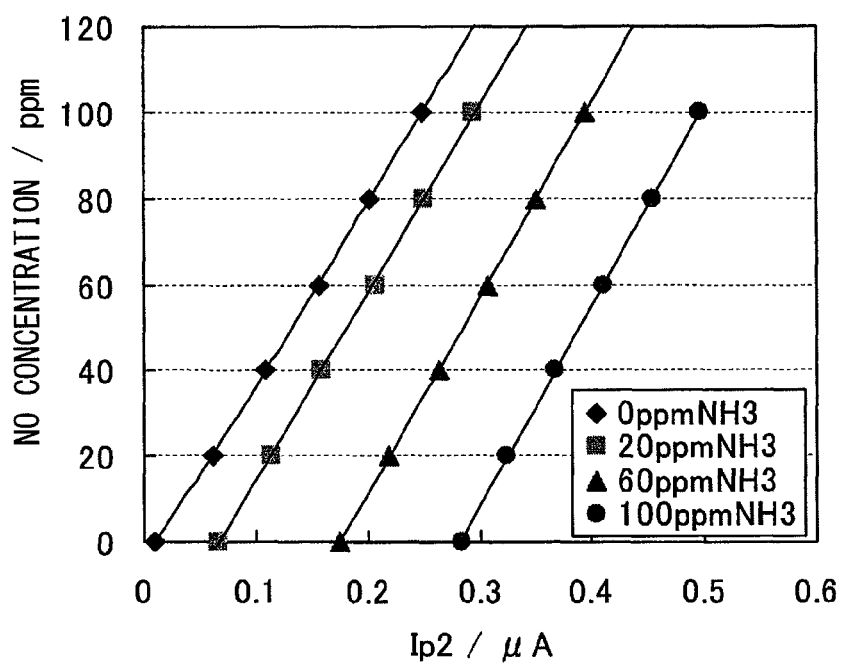
FIG. 6 is a graph showing an example expression representing the relation between second pumping current and NO concentration.

FIG. 6 shows an example expression representing the relation between the second pumping current and the NO concentration. In the present embodiment, for each of different ammonia concentrations, the NO concentration is represented by a first-order expression of Ip2. Ip2 itself changes depending on ammonia concentration. However, since the NO concentration is determined from the relational expression 63c representing the relation between the second pumping current and the NO concentration for each of a plurality of ammonia concentrations, an accurate value of the NO concentration (corresponding to the "first corrected NO concentration" of the invention) which is not affected by the ammonia concentration of the gas under measurement can be calculated.

Figure 7:
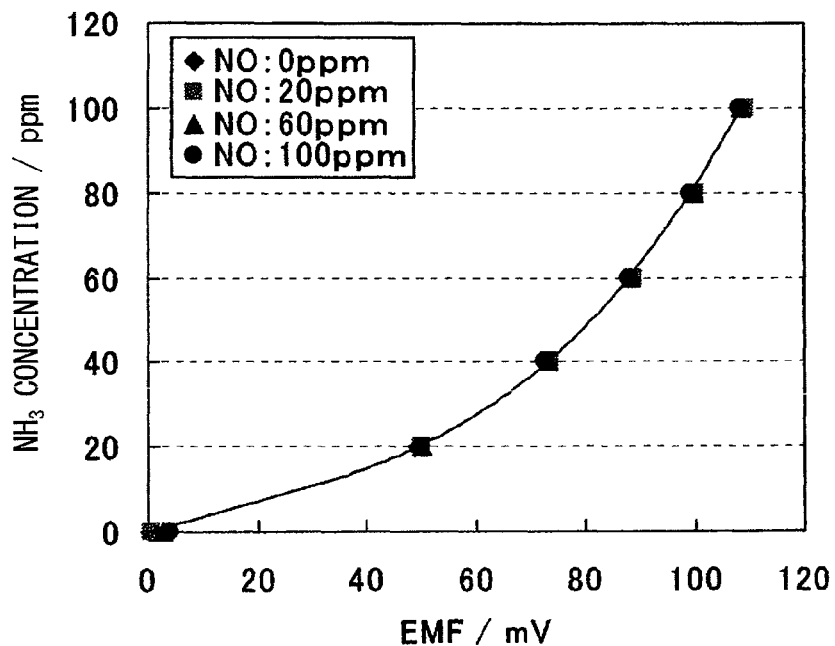
FIG. 7 is a graph showing the relation between ammonia concentration output and ammonia concentration for various NO concentrations.

As shown in FIG. 7, it has been found that the ammonia concentration calculated from the EMF is not affected by the NO concentration of the gas under measurement. Therefore, the above-mentioned corrected ammonia concentration can be directly applied to the relational expression 63c as is.

Notably, an expression representing the relation between the second pumping current and the NO concentration for a certain ammonia concentration which has not been set can be calculated, through extrapolation, from the expressions representing the relation between the second pumping current and the NO concentration for two set ammonia concentrations which are higher and lower than the certain ammonia concentration, respectively.

The relational expression 63d represents the relation between negative ammonia concentration output and $NO_2$ concentration. The relational expression makes use of a phenomenon that, in the case where the gas under measurement contains $NO_2$, when the ammonia concentration of the gas under measurement is set to 0, the ammonia concentration output of the ammonia sensor section assumes a negative value corresponding to the $NO_2$ concentration. In the case where the ammonia concentration output becomes 0 when the ammonia concentration of the gas under measurement is set to 0, the gas under measurement does not contain $NO_2$. Therefore, in such a case, as described above, the CPU 61 performs processing in which the relational expression 63c is used, rather than processing in which the relational expression 63d is used.

Figure 8:
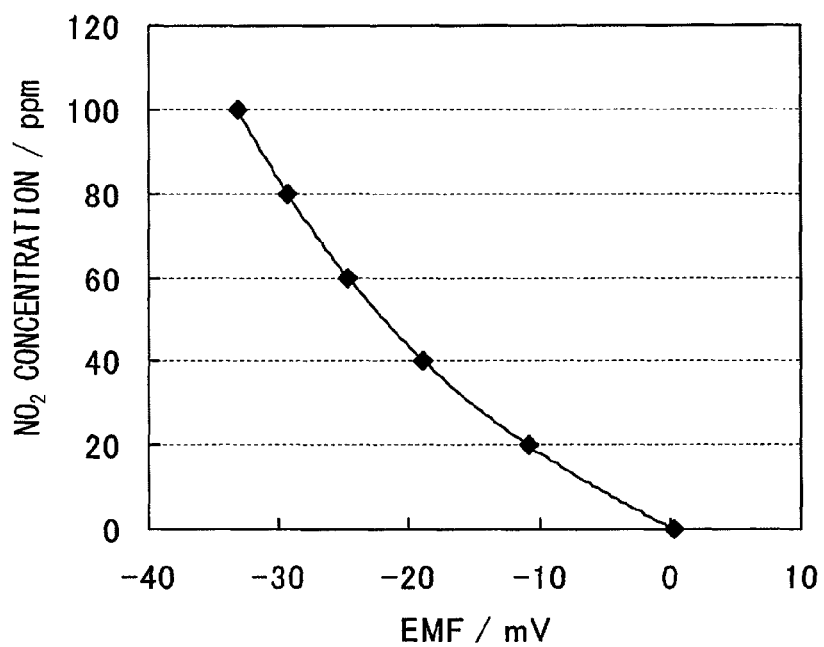
FIG. 8 is a graph showing an example expression representing the relation between negative ammonia concentration output and $NO_2$ concentration.

FIG. 8 shows an example expression representing the relation between the negative ammonia concentration output and the $NO_2$ concentration. In the present embodiment, the $NO_2$ concentration is represented by a third-order expression of the negative ammonia concentration output (EMF). When the ammonia concentration of the gas under measurement is set to 0 (e.g., when a predetermined period of time has elapsed after the injection of aqueous urea has stopped in a urea SCR (Selective Catalytic Reduction) system), the CPU detects the ammonia concentration output, and calculates the $NO_2$ concentration (corresponding to the "expected $NO_2$ concentration of the invention) of the gas under measurement by use of the relational expression 63d.

The relational expression 63e representing the relation between fractional second pumping current, and each of NO concentration and $NO_2$ concentration is an expression representing the relation between Ip2, and NO concentration and $NO_2$ concentration. This relational expression 63e is used in the case where the gas under measurement contains $NO_2$, and is used together with the relational expression 63d. The fractional second pumping current (fractional Ip2) resenting a portion (NO-attributable fraction) of the Ip2 which flows upon measurement of the gas under measurement containing NO and $NO_2$, the portion being attributable to NO, or a portion ($NO_2$-attributable fraction) of the Ip2 attributable to NO$_2$. The NO-attributable fraction and the NO$_2$-attributable fraction can be determined by measuring Ip2 in advance using a gas containing NO only and a gas containing NO$_2$ only.

Figure 9:
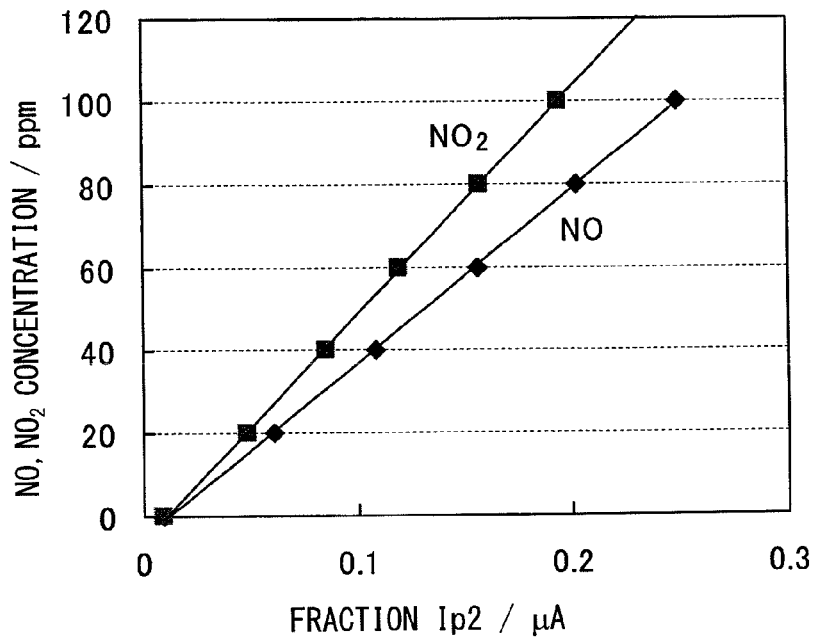
FIG. 9 is a graph showing an example expression representing the relation between fractional second pumping current, and NO concentration and $NO_2$ concentration.

FIG. 9 shows an example relational expression representing the fractional second pumping current, and the NO concentration and the NO$_2$ concentration. In the present embodiment, each of the NO concentration and the NO$_2$ concentration is represented by a first-order expression of the fractional Ip2. The NO$_2$-attributable fraction can be estimated from the relational expression 63e and the expected NO$_2$ concentration calculated from the above-described relational expression 63d. Meanwhile, since the original output of Ip2 (the total output in the case where measurement is performed using a gas containing NO and NO$_2$) is known, the NO-attributable fraction can be calculated by subtracting the NO$_2$-attributable fraction from the original Ip2 output. The NO concentration (corresponding to the "second corrected NO concentration" of the invention) can be obtained from the NO-attributable fraction and the relational expression 63e.

For example, in the case where the expected NO$_2$ concentration is 40 ppm, the NO$_2$-attributable fraction is estimated to be about 0.084 μA from the relational expression 63e. When the original output of Ip2, for example, is 0.15 μA, the NO-attributable fraction is estimated to be 0.066 μA (0.15-0.084). Then, the NO concentration is calculated to be about 22.9 ppm from the relational expression 63e.

The relational expression 63f representing the relation between ammonia concentration output and ammonia concentration is set for each combination between a plurality of oxygen concentrations and a plurality of NO$_2$ concentrations, and is a relational expression representing the relation between the ammonia concentration output of the ammonia sensor section and the ammonia concentration of the gas under measurement.

Figure 10:
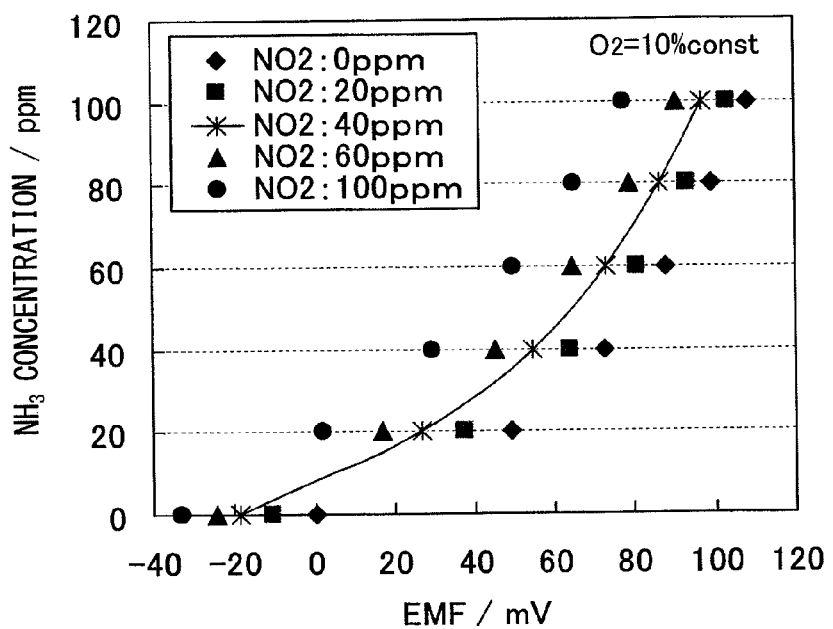
FIG. 10 is a graph showing an example expression representing the relation between ammonia concentration output and ammonia concentration at a certain oxygen concentration for various $NO_2$ concentrations.

FIG. 10 shows an example relational expression representing the relation between the ammonia concentration output and the ammonia concentration at a certain oxygen concentration (10%) for different NO$_2$ concentrations. In the present embodiment, for each of the different NO$_2$ concentrations, the ammonia concentration is represented by a third-order expression of EMF. The EMF changes depending on oxygen concentration and NO$_2$ concentration. However, since the ammonia concentration is determined from the relational expression 63f representing the relation between the ammonia concentration output and the ammonia concentration for each combination between a plurality of oxygen concentrations and a plurality of NO$_2$ concentrations, an accurate value of the ammonia concentration (corresponding to the "corrected ammonia concentration" in the invention) which is not affected by the oxygen concentration and NO$_2$ concentration of the gas under measurement can be calculated.

In order to distinguish from the "corrected ammonia concentration" calculated on the basis of the relational expression 63b, the "corrected ammonia concentration" calculated on the basis of the present relational expression 63f will be referred to as the "re-corrected ammonia concentration" as needed. The re-corrected ammonia concentration has a higher accuracy than the ammonia concentration calculated on the basis of the relational expression 63b, because the influence of the NO$_2$ concentration is taken into consideration.

Notably, an expression representing the relation between the ammonia concentration output and the ammonia concentration for a combination of a certain oxygen concentration and a certain NO$_2$ concentration which have not been set can be calculated, through extrapolation, from the expressions representing the relation between the ammonia concentration output and the ammonia concentration for two set oxygen concentrations which are higher and lower than the certain oxygen concentration, respectively, and for two set NO$_2$ concentrations which are higher and lower than the certain NO$_2$ concentration, respectively.

Figure 11A:
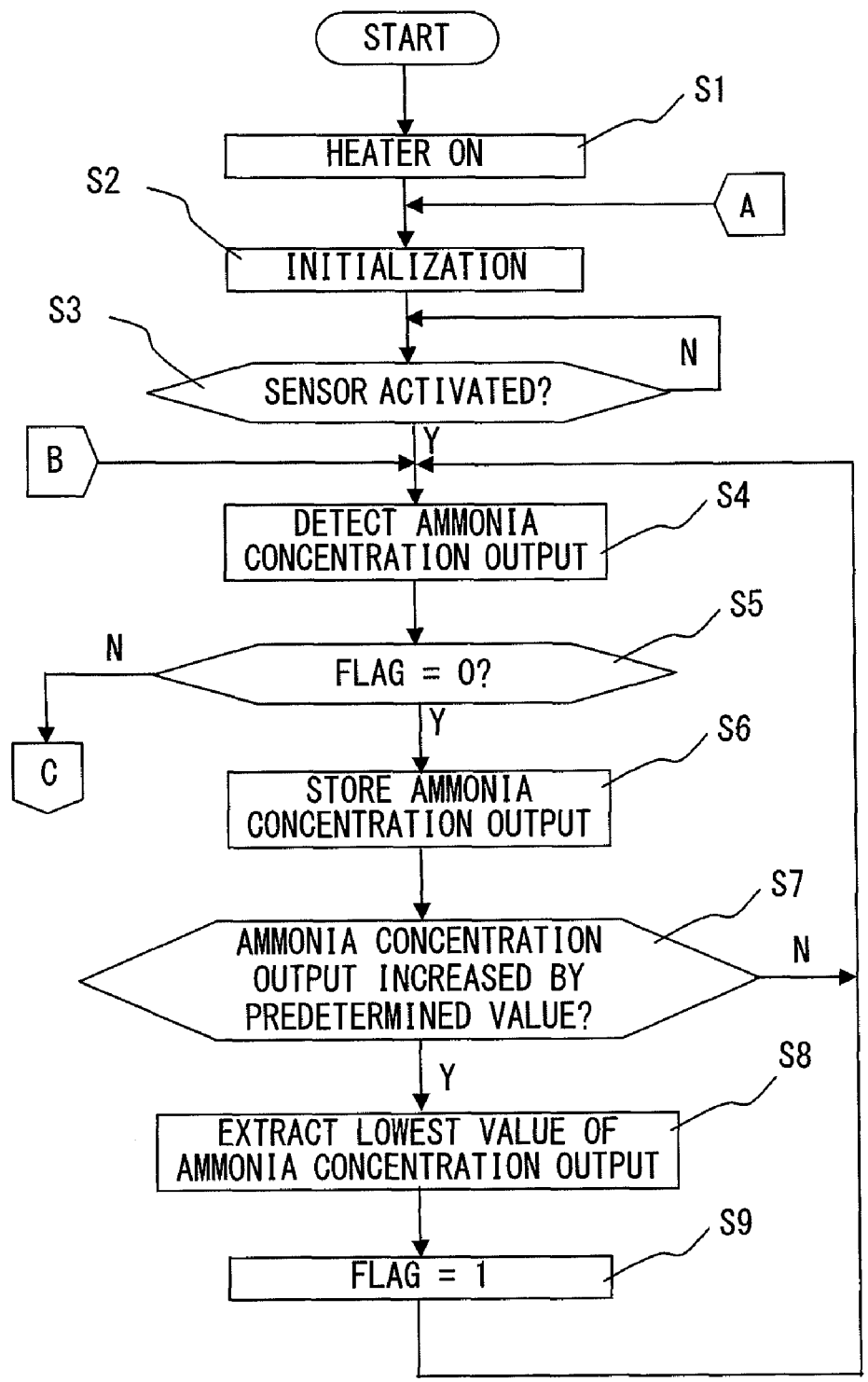
FIGS. 11A and 11B are flowcharts showing the processing performed by the gas sensor control apparatus (the microcomputer thereof) in calculating ammonia concentration and the concentration of other gas components.
Figure 11B:
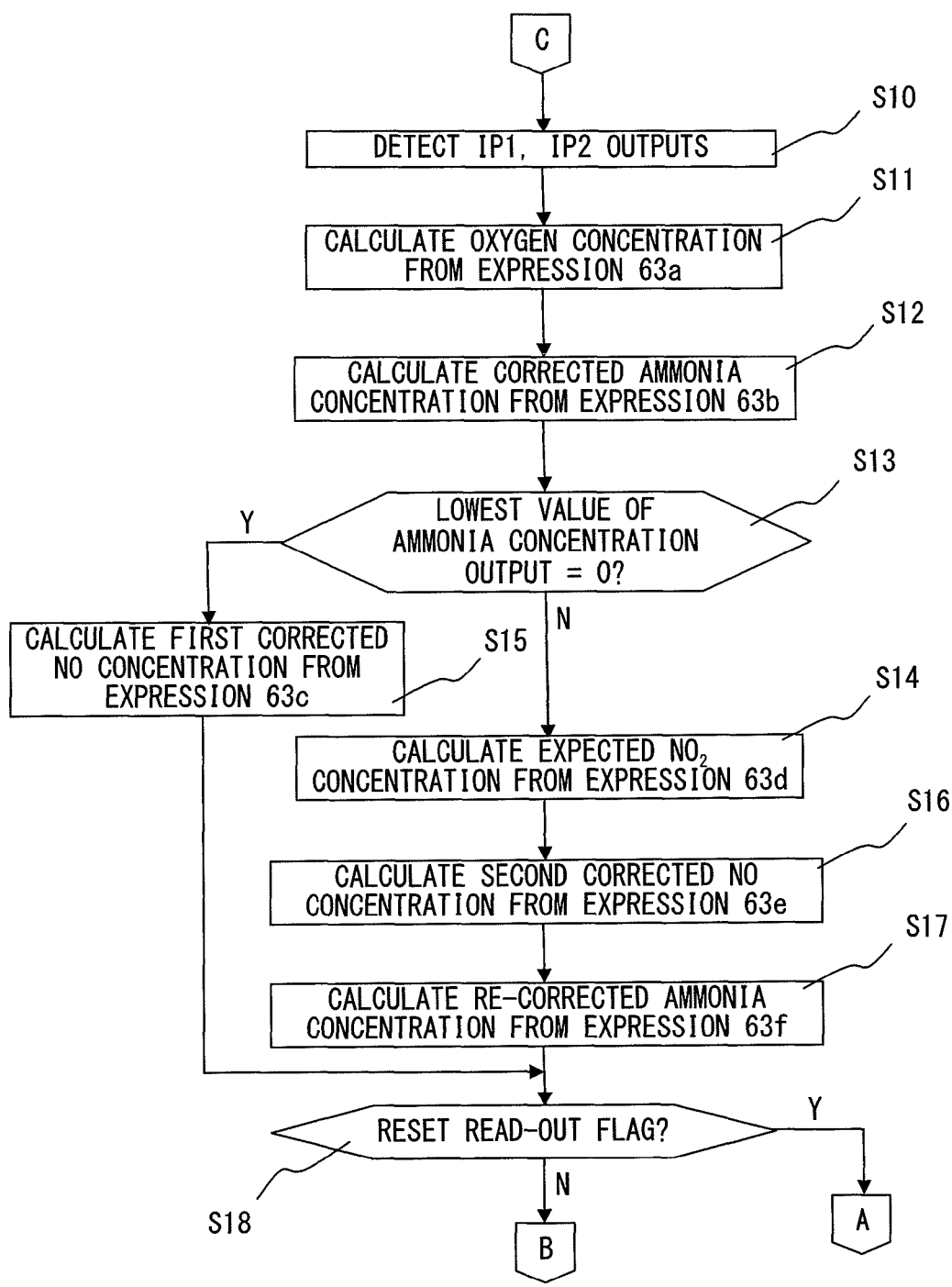

Next, with reference to FIGS. 11A and 11B, processing performed by the microcomputer 60 (CPU 61) of the multi-gas sensor control apparatus 300 in order to calculate the concentrations of various gas components of the gas under measurement will be described. Notably, the following description is made on the assumption that the multi-gas sensor 200A is disposed in a urea SCR (Selective Catalytic Reduction) system. In the urea SCR system, in order to remove NO$_X$, aqueous urea is injected depending on the detection result at the multi-gas sensor 200A. However, when NO$_X$ is determined to have been removed, the injection of aqueous urea is stopped. Accordingly, when a predetermined time has elapsed after injection of aqueous urea has stopped, the CPU 61 judges that "the ammonia concentration of the gas under measurement is 0."

First, the CPU 61 operates the heater circuit 57 to thereby cause the heater 21 to generate heat (step S1). After that, the CPU 61 performs initialization processing, whereby various values of the ammonia concentration output, the lowest value of the ammonia concentration output, and a read-out flag stored in the RAM 62 are reset (step S2). The read-out flag, which represents whether or not the lowest value of the ammonia concentration output has been read out, is set to an unestablished state. After that, the CPU 61 determines whether or not the sensor has been heated to an activation temperature by the heater 21 (step S3). In general, this determination is made by monitoring the electric resistance of the second solid electrolyte body 4a of the second pumping cell 4. The CPU 61 repeats the processing of step S3 until the heater 21 reaches the activation temperature. When the sensor has reached the activation temperature (Yes in step S3), the CPU 61 then detects the ammonia concentration output on the basis of the voltage between the above-mentioned paired electrodes 42a (step S4). Notably, in the present embodiment, since the ammonia sensor section 42 is an electromotive-force-type sensor, the ammonia concentration output is electromotive force (EMF).

Next, the CPU 61 determines whether or not the read-out flag is 0 (step S5). When the CPU 61 makes a "Yes" determination in step S5, it stores the value of the ammonia concentration output in the RAM 62 (step S6). After that, the CPU 61 determines whether or not the ammonia concentration output has increased by a predetermined value or more (step S7). Notably, the determination as to whether or not the ammonia concentration output has increased by a predetermined value or more is made by subtracting the last value of the ammonia concentration output from the value of the ammonia concentration output acquired at this time, and determining whether or not a resultant value is equal to or greater than a predetermined value (determined, in consideration of variation, from a value calculated when the ammonia concentration has clearly increased). When the CPU 61 makes a "No" determination in step S7, it returns to step S4, and repeats steps S4 to S7.

When the CPU 61 makes a "Yes" determination in step S7, the CPU 61 determines that a predetermined period of time has elapsed after the injection of aqueous urea has stopped, and extracts the ammonia concentration output at the time when the ammonia concentration of the gas under measurement is 0; i.e., the lowest value of the values of the ammonia gas concentration output stored in the RAM 62 (step S8). Subsequently, the CPU 61 sets the read-out flag to 1 (step S9), and returns to step S4.

Meanwhile, when the CPU 61 makes a "No" determination in step S5, the CPU 61 detects the first pumping current Ip1 flowing through the first pumping cell 2, and the second pumping current Ip2 flowing through the second pumping cell 4 (step S10).

Next, the CPU 61 calculates the oxygen concentration on the basis of the above-described first pumping current Ip1 and the relational expression 63*a* (step S11). Moreover, the CPU 61 calculates the corrected ammonia concentration on the basis of the oxygen concentration calculated in step S8 and the relational expression 63*b* (step S12).

Next, the CPU 61 determines whether or not the ammonia concentration output of the ammonia sensor section 42 at the "time when the ammonia concentration of the gas under measurement is set to 0" is 0 (step S13). Specifically, the CPU 61 determines whether or not the lowest value of the ammonia gas concentration output extracted in step S8 is 0. When the CPU 61 makes a "Yes" determination in step S13, the CPU 61 refers to the relational expression 63*c* corresponding to the corrected ammonia concentration calculated in step S10, and calculates the first corrected NO concentration on the basis of the referred relational expression 63*c* and the Ip2 detected in step S6 (step S15).

Notably, in the case where a "Yes" determination is made in step S13, the gas under measurement is judged not to contain $NO_2$. Accordingly, the corrected ammonia concentration calculated in step S12 and the above-mentioned first NO concentration are employed as final values of the gas components of the gas under measurement.

Meanwhile, in the case where a "No" determination is made in step S13, the CPU 61 calculates the expected $NO_2$ concentration on the basis of the ammonia concentration output of the ammonia sensor section 42 and the relational expression 63*d* (step S14). That is, in this case, since the gas under measurement contains NO and $NO_2$, both the NO concentration and the $NO_2$ concentration must be obtained.

Next, the CPU 61 performs the processing of step S16 for calculating the second corrected NO concentration. In step S16, the CPU 61 first estimates the $NO_2$-attributable fraction from the expected $NO_2$ concentration calculated in step S14 and the relational expression 63*e*. Subsequently, the CPU 61 subtracts the $NO_2$-attributable fraction from the Ip2 (original output) detected in step S10, to thereby calculate the NO-attributable fraction. Moreover, the CPU 61 calculates the second corrected NO concentration from the obtained NO-attributable fraction and the relational expression 63*e*.

Notably, in the case where a "No" determination is made in step S13, the gas under measurement contains NO and $NO_2$. Therefore, the corrected ammonia concentration calculated in step S12, the above-mentioned expected $NO_2$ concentration, and the above-mentioned second corrected NO concentration can be employed as the final values of the gas components of the gas under measurement. Notably, the CPU 61 may refer to the relational expression 63*f* corresponding to the oxygen concentration calculated in step S11, and calculate the re-corrected ammonia concentration on the basis of the referred relational expression 63*f* and the expected $NO_2$ concentration calculated in step S14 (step S17).

In this case, in place of the corrected ammonia concentration calculated in step S12, the re-corrected ammonia concentration calculated in step S17 is employed.

The CPU 61 then outputs to the ECU 400 the gas concentrations calculated in the respective steps. After that, the CPU 61 determines whether to reset the read-out flag (step S18). That is, the CPU 61 determines whether to replace the lowest value of the ammonia concentration output extracted in step S8 with the lowest value of the ammonia concentration output obtained for the second time, immediately before the predetermined period of time has elapsed for the second time after the injection of aqueous urea has stopped. When the CPU 61 makes a "No" determination in step S18, the CPU 61 repeats steps S4, S5, and S10 to S18. When the CPU 61 makes a "Yes" determination in step S18, the CPU 61 repeats steps S1 to S18.

Notably, the above-mentioned processing ends when operation of the internal combustion engine stops.

Notably, the CPU 61, which performs the processing of steps S4 to S18, corresponds to the "control means" of the invention. In the present embodiment, the control method in the microcomputer 60 has been described. However, the entirety or a portion of the present control can be performed in the ECU 400.

As described above, in the present invention, the $NO_X$ sensor section 30A and the ammonia sensor section 42 are provided in the single multi-gas sensor 200A, and are placed under measurement environments which are substantially the same (in terms of the composition, concentration, temperature, flow rate, pressure, etc., of the gas under measurement). Therefore, a drop in gas detection accuracy is suppressed, which drop would otherwise occur due to a difference in measurement environment.

That is, by providing the $NO_X$ sensor section 30A and the ammonia sensor section 42 on the single multi-gas sensor 200A, the $NO_X$ (NO and $NO_2$) concentrations and the ammonia concentration can be simultaneously measured without being affected by the measurement environment, whereby accuracy in detecting the $NO_X$ concentration and the ammonia concentration is improved. Also, since the gas under measurement comes into contact with the single multi-gas sensor 200A, $NO_X$ and ammonia can be detected substantially simultaneously, whereby a drop in detection accuracy stemming from a time lag between the detection of $NO_X$ and the detection of ammonia can be suppressed.

Moreover, the cost and size of the sensor of the present invention can be reduced, as compared with the case where the $NO_X$ sensor section 30A and the ammonia sensor section 42 are separate sensors.

The multi-gas sensor 200A of the present invention can be used, for example, for detection of deterioration of catalyst provided as an auxiliary device of an engine apparatus main body, optimization of the urea injection amount in a urea SCR system, and accurate measurement of gas components ($NO_X$, ammonia) on the downstream side of the catalyst. For example, in the case where only the $NO_X$ sensor is used for sensing of the apparatus, when ammonia is discharged from the downstream side of the catalyst, it has been impossible to clearly distinguish between (i) discharge of ammonia due to excessive addition of urea, (ii) discharge of $NO_X$ due to too little addition of urea, and (iii) discharge of ammonia due to deterioration of the SCR catalyst. In contrast, when the multi-gas sensor of the present invention is used, these phenomena can be distinguished from one another.

The multi-gas sensor 200A of the present invention can be manufactured in a manner similar to the manner of manufacture of known $NO_X$ sensors and ammonia sensors. For example, as in the case of known $NO_X$ sensors, the solid electrolyte bodies of the $NO_X$ sensor section are formed from a green sheet, and respective electrodes, leads, and insulating layers are formed through paste printing, whereby a green body of the $NO_X$ sensor section is formed. Subsequently, a green body of the ammonia sensor section is formed on the surface of the green body of the $NO_X$ sensor section at a predetermined position. The green body of the ammonia sensor section can be formed by paste printing of the electrodes, leads, sensitive portion, solid electrolyte body, diffusion layer, etc., of the sensor section.

The green body of the $NO_X$ sensor section with the green body of the ammonia sensor section formed on the surface thereof is fired at a predetermined temperature, whereby the sensor element section of the multi-gas sensor is manufactured. The manufactured sensor element section is assembled to the housing, whereby the multi-gas sensor can be obtained.

The present invention is not limited to the above-described embodiment, and encompasses various modifications and equivalents which fall within the scope of the present invention. For example, in the above-described embodiment, the number of solid electrolyte bodies (layers) which constitute the $NO_X$ sensor section 30A is three; however, the number of the solid electrolyte bodies (layers) may be two. For example, the element structure of an $NO_X$ sensor section formed by two solid electrolyte bodies (layers) is described in Japanese Patent Application Laid-Open (kokai) No. 2004-354400 (FIG. 3).

In this case, the second measurement chamber S2 is defined between the solid electrolyte bodies 2a and 6a in FIG. 2, and the first measurement chamber S1 and the second measurement chamber S2 are separated from each other by the second diffusion resistance 8b. The inner second pumping electrode 4b is disposed on the upper surface of the solid electrolyte body 6. A portion of the lower surface of the solid electrolyte body 6 is exposed to the outside, and the second pumping counter electrode 4c is disposed on the exposed portion of the lower surface.

In the above-described embodiment, the determination of step S13 is performed after the corrected ammonia concentration is calculated from the relational expression 63b (step S12). However, the determination of step S13 may be performed before step S12.

In the latter case, when a "No" determination is made in step S13, ammonia concentration is calculated in step S17 without performing step S12. Therefore, it becomes unnecessary to execute the processing of step S12. When a "Yes" determination is made in step S13, the processing of step S12 is performed.

EXAMPLES (1) Manufacture of Sensor

A multi-gas sensor 200A according to the above-described embodiment was manufactured. The paired electrodes 42a of the electromotive-force-type ammonia sensor section 42; i.e., the detection electrode 42a1 and the reference electrode 42a2, were mainly formed of gold and platinum, respectively. The selective reaction layer 42b was formed of $BiVO_4$. Further, a porous layer of spinel ($MgAl_2O_4$) was formed as the diffusion layer 44B covering the paired electrodes 42a and the selective reaction layer 42b.

Example 1

(2) Evaluation of Sensor Characteristics for the Case Where NO and $NO_2$ Co-Exist 2-1 Calculation of Ammonia Concentration First, the value of Ip1 was measured in advance within a plurality of gases having known different $O_2$ concentrations, and the relational expression 63a, which is a first-order expression, was prepared. Similarly, the value of EMF corresponding to each of known different ammonia concentrations was obtained within a plurality of gases having known different $O_2$ concentrations, whereby the relational expression 63b shown in FIG. 5 was prepared.

Next, evaluation of sensor characteristics was performed using a model gas generator. The gas composition of the model gas generator was set such that $NH_3$=50 ppm; $O_2$=1%, 5%, or 10%; $CO_2$=5%; $H_2O$=5%; and $N_2$=bal (balance). The gas temperature was set to 280° C., the gas flow rate was set to 5 m/s, and the controlled temperature at the center between the paired electrodes of the ammonia sensor section 42 was set to 650° C.

The multi-gas sensor was disposed in a gas flow of the model gas generator, and the first pumping current (Ip1) of the first pumping cell 2 and the ammonia concentration output (EMF) of the ammonia sensor section 42 were detected, while the $O_2$ concentration of the gas flow was respectively changed to 1%, 5%, and 10%.

The $O_2$ concentration of the model gas was calculated on the basis of the relational expression 63a and Ip1. The calculated $O_2$ concentration was 1%, 5% and 10%, which are equal to the concentrations of $O_2$ introduced into the base gas. The ammonia concentration was calculated using the $O_2$ concentrations, the relational expression 63b, and the EMF. The results of the calculation are shown in Table 1 as Example 1.

TABLE 1

| | Calculated ammonia concentration (ppm) | | |
| --- | --- | --- | --- |
| | $O_2$ = 1% | $O_2$ = 5% | $O_2$ = 10% |
| Example 1 | 50.8 | 50.3 | 50.3 |

Table 1 shows that, in the case of Example 1 in which the ammonia concentration was calculated in consideration of the $O_2$ concentration of the model gas, the ammonia concentration was accurately calculated without being affected by the $O_2$ concentration.

2-2 Calculation of NO Concentration and $NO_2$ Concentration

First, the ammonia concentration was set to 0, and a negative value of EMF was measured in advance in a plurality of gases having known different $NO_2$ concentrations, whereby the relational expression 63d shown in FIG. 8 was prepared. Also, a value of Ip2 ($NO_2$-attributable fraction) was obtained in a plurality of gases containing $NO_2$ only and having known different $NO_2$ concentrations. Similarly, a value of Ip2 (NO-attributable fraction) was obtained in a plurality of gases containing NO only and having known different NO concentrations. Through these procedures, the relational expression 63e shown in FIG. 9 was prepared.

Furthermore, the $NO_2$ concentration of a gas having a known constant $O_2$ concentration was set to a predetermined value, and values of the EMF corresponding to known ammonia concentrations were obtained. This procedure was repeated for various $NO_2$ concentrations, whereby the relational expression 63f shown in FIG. 10 was prepared. Also, the relational expression 63f was similarly prepared while the $O_2$ concentration was changed. Finally, the relational expression 63f representing values of the EMF corresponding to various ammonia concentrations for each combination between different $O_2$ concentrations and different $NO_2$ concentrations was obtained.

Next, the sensor was disposed in a gas flow of the model gas generator under the same conditions as those mentioned in the section 2-1, except for the gas composition. Notably, a gas was used which contained $NH_3$, NO, $NO_2$ in predetermined amounts and whose composition was set such that $O_2$=10%; $CO_2$=5%; $H_2O$=5%; and $N_2$=bal.

When the EMF was detected while the $NH_3$ concentration of the base gas was set to 0 ppm, the detected EMF was −19 mV. The expected $NO_2$ concentration calculated from this value of EMF by use of the relational expression 63d of FIG. 8 was 40 ppm. The $NO_2$-attributable fraction estimated by use of the expected $NO_2$ concentration and the relational expression 63e of FIG. 9 was 0.084 μA.

Meanwhile, the second pumping current (Ip2) of the second pumping cell 4 detected in this base gas was 0.15 μA.

Accordingly, the NO-attributable fraction was estimated to be 0.066 μA (0.15-0.084). The NO concentration calculated from this NO-attributable fraction and the relational expression 63e was 22.9 ppm.

2-3 Calculation of Ammonia Concentration Under Coexistence of NO and $NO_2$

The sensor was attached to the model gas generator described in paragraph 2-2 above, and the EMF was detected in the above-described gas. The detected EMF was 64.7 mV. Then, the ammonia concentration at $NO_2$=40 ppm was calculated using the relational expression 63f of FIG. 10 for the case of $O_2$=10%. The calculated ammonia concentration was 50.1 ppm.

Irrespective of coexistence of NO and $NO_2$ in the model gas, the NO concentration and the $NO_2$ concentration could be separately calculated. In general, in conventional $NO_x$ sensors, separation of NO and $NO_2$ is difficult. In addition, NO and $NO_2$ differ in molecular size. Therefore, even in the case where the Ip2 output of the $NO_x$ sensor is the same, the calculated $NO_x$ concentration may change in accordance with the ratio between NO and $NO_2$ in the gas under measurement. In contrast, in Example 1, the NO concentration and the $NO_2$ concentration were calculated separately and accurately.

Moreover, when the ammonia concentration was calculated in consideration of not only the $O_2$ concentration but also the $NO_2$ concentration, the accuracy was further improved as compared with the case where the ammonia concentration was calculated in consideration of the $O_2$ concentration only (Table 1).

Example 2

(3) Evaluation of Sensor Characteristics for the Case where the Gas Contains NO but does not Contain $NO_2$ 3-1 Calculation of Ammonia Concentration The calculation of ammonia concentration was performed in the same manner as described in paragraph 2-1, and the results shown in Table 1 were obtained.

3-2 Calculation of NO Concentration

First, values of the Ip2 corresponding to known NO concentrations were obtained in a plurality of gases having known different $NH_3$ concentrations, and the relational expression 63c shown in FIG. 6 was prepared.

Next, the sensor was disposed in a gas flow of the model gas generator under the same conditions as those described in paragraph 2-1, except that the gas composition was set such that $NH_3$=0 ppm, 20 ppm, 60 ppm, or 100 ppm; NO=50 ppm; $O_2$=10%; $CO_2$=5%; $H_2O$=5%; and $N_2$=bal.

Ip2 was detected in a state in which the sensor was placed in the above-mentioned gas, and the NO concentration was calculated using the relational expression 63c shown in FIG. 6. The results are shown in Table 2. Notably, the $NH_3$ concentration of the base gas was changed to 0 ppm, 20 ppm, 60 ppm, and 100 ppm, and, of the relational expressions 63c shown in FIG. 6, a first-order expression corresponding to the ammonia concentration was used.

TABLE 2

| | Calculated NO concentration (ppm) | | | |
|---|---|---|---|---|
| | $NH_3$ = 0 ppm | $NH_3$ = 20 ppm | $NH_3$ = 60 ppm | $NH_3$ = 100 ppm |
| Example 2 | 49.9 | 50 | 49.9 | 50.1 |

Table 2 shows that, in the case of Example 2 in which the NO concentration was calculated in consideration of the ammonia concentration of the model gas, the NO concentration was accurately calculated without being affected by the ammonia concentration.

It should further be apparent to those skilled in the art that various changes in form and detail of the invention as shown and described above may be made. It is intended that such changes be included within the spirit and scope of the claims appended hereto.

This application claims priority from Japanese Patent Application No. JP 2009-203303 filed Sep. 3, 2009, incorporated herein by reference in its entirety.

What is claimed is:

1. A method for controlling a multi-gas sensor, the multi-gas sensor comprising an $NO_x$ sensor section; and an ammonia sensor section formed on an outer surface of the $NO_x$ sensor section, wherein the $NO_x$ sensor section includes a first pumping cell which has paired first electrodes provided on a first solid electrolyte body such that the paired first electrodes are located on both the interior and exterior of a first measurement chamber, respectively, and is adapted to pump oxygen into or out of a gas under measurement introduced into the first measurement chamber, and a second pumping cell which, has paired second electrodes provided on a second solid electrolyte body such that the paired second electrodes are located on both the interior and exterior of an $NO_x$ measurement chamber communicating with the first measurement chamber, respectively, and is configured such that a second pumping current flows between the paired second electrodes, the second pumping current corresponding to an $NO_x$ concentration of the gas under measurement having flowed into the $NO_x$ measurement chamber after adjustment of its oxygen concentration in the first measurement chamber; and the ammonia sensor section has a solid electrolyte body and at least a pair of electrodes formed on a side of the solid electrolyte body opposite the $NO_x$ sensor section and outputs an ammonia concentration output, wherein the solid electrolyte body of the ammonia sensor section is insulated from the $NO_x$ sensor section by an insulating layer, the method comprising calculating an oxygen concentration on the basis of a first pumping current flowing through the first pumping cell; and calculating a corrected ammonia concentration on the basis of the oxygen concentration and the ammonia concentration output of the ammonia sensor section.

2. The method for controlling a multi-gas sensor according to claim 1, wherein, in the case where the ammonia concentration output of the ammonia sensor section becomes 0 as a result of setting the ammonia concentration of the gas under measurement to 0, said method comprises calculating a first corrected NO concentration on the basis of the corrected ammonia concentration and the second pumping current.

3. The method for controlling a multi-gas sensor according to claim 1, wherein, in the case where the ammonia concentration output of the ammonia sensor section becomes negative as a result of setting the ammonia concentration of the gas under measurement to 0, said method comprises calculating an expected $NO_2$ concentration in advance on the basis of the negative ammonia concentration output, and calculating a second corrected NO concentration on the basis of the second pumping current and the expected $NO_2$ concentration.

4. The method for controlling a multi-gas sensor according to claim 3, which comprises calculating the corrected ammonia concentration on the basis of the expected $NO_2$ concentration as well as the oxygen concentration.

5. An apparatus for controlling a multi-gas sensor, said multi-gas sensor comprising an $NO_x$ sensor section; and an ammonia sensor section formed on an outer surface of the $NO_x$ sensor section, wherein the $NO_x$ sensor section includes a first pumping cell which has paired first electrodes provided on a first solid electrolyte body such that the paired first electrodes are located on both the interior and exterior of a first measurement chamber, respectively, and is adapted to pump oxygen into or out of a gas under measurement introduced into the first measurement chamber, and a second pumping cell which has paired second electrodes provided on a second solid electrolyte body such that the paired second electrodes are located on both the interior and exterior of an $NO_x$ measurement chamber communicating with the first measurement chamber, respectively, and is configured such that a second pumping current flows between the paired second electrodes, the second pumping current corresponding to an $NO_x$ concentration of the gas under measurement having flowed into the $NO_x$ measurement chamber after adjustment of its oxygen concentration in the first measurement chamber; and the ammonia sensor section has a solid electrolyte body and at least a pair of electrodes formed on a side of the solid electrolyte body opposite the $NO_x$ sensor section and outputs an ammonia concentration output, wherein the solid electrolyte body of the ammonia sensor section is insulated from the NO sensor section b an insulating layer, the apparatus comprising control means for calculating an oxygen concentration on the basis of a first pumping current flowing through the first pumping cell, and for calculating a corrected ammonia concentration on the basis of the oxygen concentration and the ammonia concentration output of the ammonia sensor section.

* * * * *